US012653410B2

(12) United States Patent
Wang et al.

(10) Patent No.: US 12,653,410 B2
(45) Date of Patent: Jun. 16, 2026

(54) HEART MEASUREMENT USING ACOUSTIC TECHNIQUES

(71) Applicant: Apple Inc., Cupertino, CA (US)

(72) Inventors: Avery L. Wang, Palo Alto, CA (US); Tom-Davy W. Saux, Los Altos, CA (US)

(73) Assignee: Apple Inc., Cupertino, CA (US)

( * ) Notice: Subject to any disclaimer, the term of this patent is extended or adjusted under 35 U.S.C. 154(b) by 290 days.

(21) Appl. No.: 18/460,457

(22) Filed: Sep. 1, 2023

(65) Prior Publication Data

US 2024/0099599 A1 Mar. 28, 2024

Related U.S. Application Data

(60) Provisional application No. 63/376,349, filed on Sep. 20, 2022.

(51) Int. Cl.
*A61B 5/00* (2006.01)
*A61B 5/024* (2006.01)
*H04R 1/10* (2006.01)

(52) U.S. Cl.
CPC ........ *A61B 5/02438* (2013.01); *A61B 5/6815* (2013.01); *H04R 1/1091* (2013.01); *A61B 2562/0204* (2013.01)

(58) Field of Classification Search
CPC . A61B 5/02438; A61B 5/6815; A61B 5/1102; A61B 2562/0204; H04R 3/00; G01H 9/00
See application file for complete search history.

(56) References Cited

U.S. PATENT DOCUMENTS

| | | | |
|---|---|---|---|
| 11,051,702 B2 | 7/2021 | Lin et al. | |
| 2010/0125218 A1* | 5/2010 | Haartsen | A61B 5/6817 |
| | | | 600/528 |
| 2011/0213263 A1 | 9/2011 | Haartsen | |
| 2013/0109949 A1 | 5/2013 | Li et al. | |
| 2017/0070834 A1 | 3/2017 | Ben-Ami et al. | |
| 2017/0105622 A1 | 4/2017 | Boesen et al. | |
| 2020/0187795 A1 | 6/2020 | Yokoi et al. | |
| 2020/0367810 A1 | 11/2020 | Shouldice et al. | |

(Continued)

FOREIGN PATENT DOCUMENTS

| | | | | | |
|---|---|---|---|---|---|
| CN | 108391207 A | * | 8/2017 | .............. | H04R 3/12 |
| GB | 2598042 A | | 2/2022 | | |

(Continued)

OTHER PUBLICATIONS

Alkhodari et al., "Deep Learning Predicts Heart Failure With Preserved, Mid-Range, and Reduced Left Ventricular Ejection Fraction From Patient Clinical Profiles", received from https://www.frontiersin.org/articles/10.3389/fcvm.2021.755968/full, Nov. 22, 2021, 13 pages.

(Continued)

*Primary Examiner* — Sana Sahand
(74) *Attorney, Agent, or Firm* — Aikin & Gallant, LLP

(57) ABSTRACT

An ultrasonic wave is output from a speaker of a head-worn device. A microphone signal is obtained from a microphone of the head-worn device that senses the ultrasonic wave as it reflects off an ear of a user. Heart activity such as a heart rate of the user is determined based at least on the microphone signal. Other aspects are also described and claimed.

20 Claims, 8 Drawing Sheets

(56) References Cited

U.S. PATENT DOCUMENTS

| 2021/0275056 A1 | 9/2021 | McMahon et al. |
| 2022/0095049 A1 | 3/2022 | Podhajny et al. |
| 2022/0183659 A1 | 6/2022 | Margalit |

FOREIGN PATENT DOCUMENTS

| KR | 20210012417 A | 2/2021 | | |
| WO | 2017035636 A1 | 3/2017 | | |
| WO | WO-2022013566 A1 * | 1/2022 | ........... | A61B 5/6817 |
| WO | 2023240224 A1 | 12/2023 | | |
| WO | 2023240233 A1 | 12/2023 | | |
| WO | 2023240240 A1 | 12/2023 | | |

OTHER PUBLICATIONS

Wang et al., "Using smart speakers to contactlessly monitor heart rhythms", received from https://www.nature.com/articles/s42003-021-01824-9, Mar. 9, 2021, 12 pages.
Mark A. Richards, "Fundamentals of Radar Signal Processing" received from https://mhebooklibrary.com/doi/book/10.1036/0071444742?contentTab=true, Jun. 2005, 8 pages.
GB2314343.1, Combined Search and Examination Report under Sections 17 and 18(3) mailed Feb. 6, 2024, 6 pages.
GB2314343.1, "Great Britain Examination Report under Section 18(3)", mailed Oct. 7, 2024, 2 pages.

* cited by examiner

PHASE DIFFERENCE $\Delta\tilde{\phi}_m(n)$ AT 31.5 KHZ

500

Quotient Phase, Chirp Length = 0.005s

Quotient mag 0.005s

CQ Power 0.005s

HEART MEASUREMENT USING ACOUSTIC TECHNIQUES

This nonprovisional patent application claims the benefit of the earlier filing date of U.S. provisional application No. 63/376,349 filed Sep. 20, 2022.

BACKGROUND

The human heart is the primary organ of the circulatory system that pumps blood through the human body. The human heart includes four main chambers that work in a synchronized manner to circulate blood through the body. Heart movement such as contraction of the left or right atrium and ventricle, and movement of blood through the heart may be referred to as heart activity. The heart activity may include the cardiac cycle of the heart (e.g., a heartbeat), which indicates the phases of heart relaxation (diastole) and contraction (systole). Heart activity may be indicative of a person's health such as a risk or predisposition towards a heart pathology.

Heart pathologies includes a range of conditions that relate to a person's heart, such as, for example, blood vessel disease (e.g., coronary artery disease), heart rhythm problems (e.g., arrhythmias), heart defects (e.g., congenital heart defects), heart valve disease, disease of the heart muscle, heart infection, or other heart pathologies. The number of times the heart beats within a certain time period (e.g., in a minute) may be referred to as a heart rate. A person's heart rate may indicate heart fitness, heart pathology, and health of the circulatory system.

SUMMARY

In one aspect, a computing device includes a processing device (e.g., a processor) configured to cause an ultrasonic wave to output from a speaker of a head-worn device when the head-worn device is worn on or in an ear of a user, obtain a microphone signal of a microphone of the head-worn device that receives a reflected ultrasonic wave responsive to the outputted ultrasonic wave, and determine a heart activity (e.g., a heart rate) of the user of the head-worn device, based at least on the microphone signal. For example, the ultrasonic wave may reflect off of a user's ear canal, the eardrum, pinna, and/or other surfaces of the ear.

Determining the heart activity of the user may include detecting a change in phase of the ultrasonic wave in the microphone signal over time. The change in phase may be correlated to a change in path length of the ultrasonic wave from the speaker to the microphone that is due to movement of the surface of the ear where the ultrasonic wave is reflected. In turn, the change in path length may be correlated to the heart activity of the user. As such, the phase change may be correlated to a change in path length of the ultrasonic wave (e.g., shortening and lengthening), which may be caused by blood pumping through the user's body that results in a rising or falling of surface of the ear.

In some examples, the microphone may be positioned inside an ear canal of the user when the user wears the head-worn device. For example, the head-worn device may include an earbud that houses the speaker and the microphone. The speaker is driven to output the ultrasonic wave, and the microphone senses the reflected ultrasonic waves.

In some examples, the head-worn device may be worn in (or over) an ear of the user. When worn in (or over) the ear, the microphone is positioned to sufficiently receive the reflected ultrasonic wave from the ear.

In some examples, determining the heart activity may include heterodyning the reflected ultrasonic wave to generate a heterodyned signal with near-zero frequency, wherein the heterodyned signal includes a relative phase between the outputted ultrasonic wave and the reflected ultrasonic wave, or a sensed time of flight between the outputted ultrasonic wave and the reflected ultrasonic wave, or a transfer function between the outputted ultrasonic wave and the reflected ultrasonic wave. A probe signal may include a sum of at least one sinusoid, which may also be referred to as probe tones. Each sinusoid may be fixed in frequency, or it may have a time-varying frequency. To output the audio content and the ultrasonic wave through the speaker, the probe signal may be combined with an audio signal containing audio content (e.g., a song, a soundtrack, a podcast, audio of an audiovisual work, a telephone call, etc.). As such, the heart activity of the user may be determined under normal use of the head-worn device.

In some examples, determining the heart activity of the user includes applying a machine learning algorithm to the microphone signal to determine the heart activity of the user. The machine learning algorithm may be trained to correlate changes in phase of the sensed ultrasonic signal to heart activity.

In some examples, determining the heart activity of the user includes processing the microphone signal with a low pass filter. The low pass filter may be applied to a combination of the microphone signal and the probe signal (e.g., a heterodyned signal), and filter out all components other than heart activity (e.g., a heart rate).

Determining the heart activity may include detecting peaks of the heart activity sensed in the microphone signal to determine a heart rate. Heart activity (e.g., heart movement) may cause various twitches on the surface of the ear, while peaks of the heart activity may indicate a full cycle (e.g., a heartbeat).

In some aspects, the computing device is separate from the head-worn device. For example, the computing device may be communicatively coupled to the head-worn device (e.g., through one or more electric conductors or through a wireless transmitter and receiver). The computing device may be a companion device to the head-worn device, such as a smartphone, a computer, a tablet computer, a smart speaker, a server, or other computing device.

In other examples, the computing device is integral to the head-worn device. For example, in one aspect, a head-worn device includes a speaker and a microphone. The head-worn device also includes a processor configured to cause an ultrasonic wave to output from the speaker, obtain a microphone signal generated from the microphone that senses the ultrasonic wave as it reflects off an ear of the user, and determine a heart activity of the user of the head-worn device, based at least on the microphone signal.

The heart activity may be determined without use of an additional sensor. For example, the heart activity may be determined based on the microphone signal without an accelerometer, a Photoplethysmography (PPG) sensor, or any other sensor.

The determined heart activity may be stored in computer-readable memory (e.g., non-volatile computer-readable memory) and used for various purposes. The heart activity (e.g., a heart rate) may be presented to a user on a display and/or as an audible message (e.g., through a speaker of the device). The display may be integral to the head-worn device, or separate. In some aspects, the heart activity may be used to detect a risk or indication of one or more heart pathologies. Other technical features may be readily apparent to one skilled in the art from the following figures, descriptions, and claims.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Heart activity may include heart movement such as contraction of the left or right atrium and ventricle, and movement of blood through the heart. The heart activity may include the cardiac cycle of the heart (e.g., a heartbeat), which indicates the phases of heart relaxation (diastole) and contraction (systole). Under normal heart activity, the ventricular diastole begins with isovolumic relaxation, then proceeds through three sub-stages of inflow, namely: rapid inflow, diastasis, and atrial systole. Heart activity may indicate an underlying heart pathology or risk of a heart pathology. Heart pathology may include a disease or abnormality of the heart that may result in a reduced ability of the heart to effectively pump blood through the human body. Such heart pathology may be identified by or associated with irregular heart activity.

Earphones, headphones, and other hearing devices may be used for listening to music, noise cancellation and/or hearing enhancement. In some aspects of the present disclosure, these devices may be equipped with acoustic transducers (e.g., microphones) that are arranged to capture sounds inside the ear (e.g., in a user's ear canal). In some examples, the same or different microphones may be used for active noise cancellation, transparency, and adaptive equalization. Acoustic transducers may sense sound (e.g., vibrations) and generate a signal (e.g., a microphone signal) that varies in magnitude over time and/or frequency.

Further, sensors of these devices may pick up body sounds such as respiration rate, heart beats and chewing sounds. The role of earphones, headphones, or other hearing devices may be expanded to support the creation of a phonocardiogram and ballistocardiograph.

A head-worn device may include one or microphones and one or more speakers that are located in an ear of a user (e.g., a wearer of the device). One or more of the speakers may output an ultrasonic wave, which is inaudible to the human ear. The microphones may sense acoustic energy in its surroundings, such as how the ultrasonic waves output by the speakers reflect off of one or more surfaces of the user's ear. This sensed acoustic energy may be characterized in a microphone signal generated by each microphone. The microphone signal may be processed to determine changes in the sensed ultrasonic waves, which may be correlated to movements in the user's ear, which, in turn, may be analyzed to determine the user's heart activity.

Figure 1:
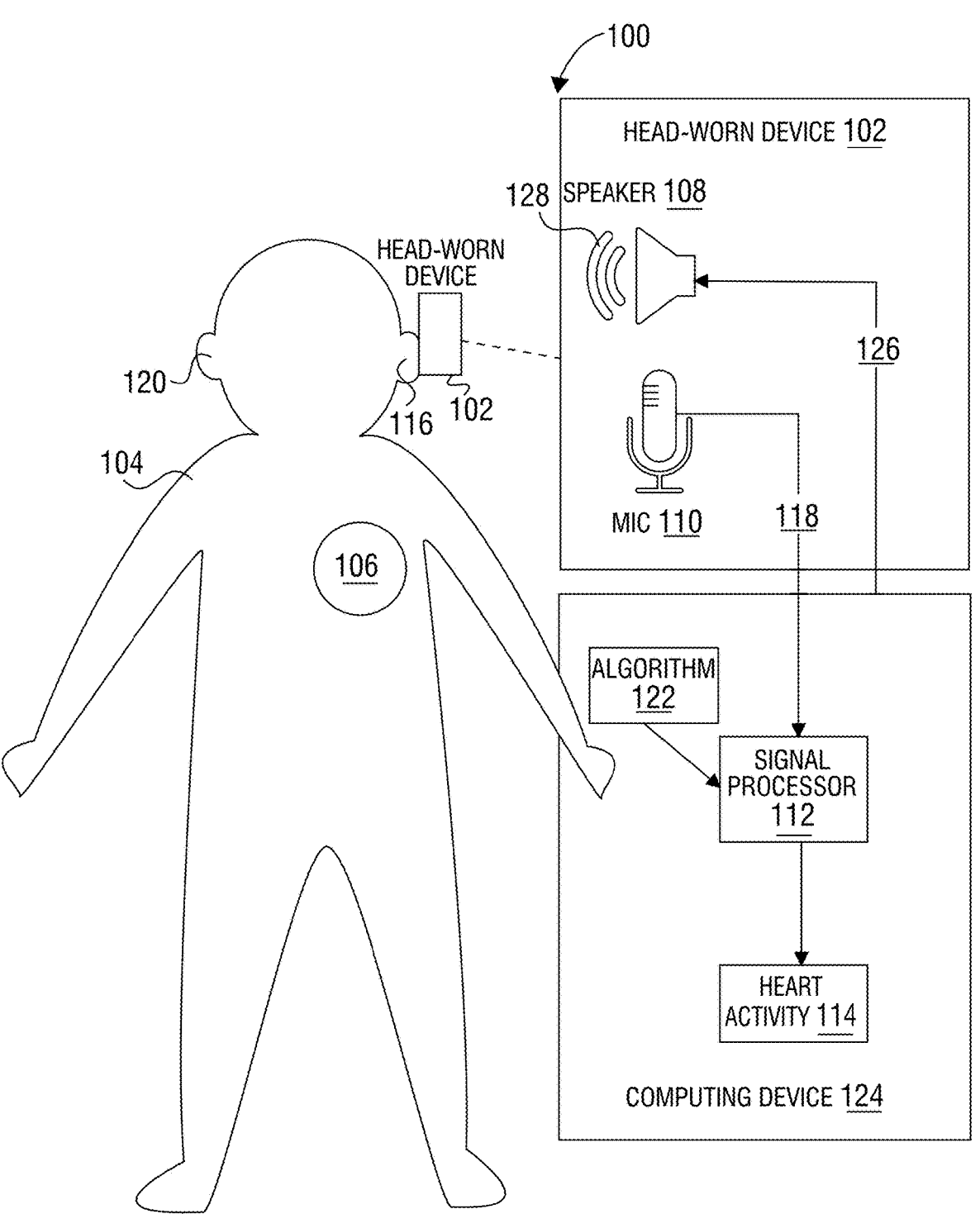
FIG. 1 shows a system for using a head-worn device to detect heart activity, in accordance with some aspects.

FIG. 1 shows a system 100 for using a head-worn device 102 to detect heart activity, in accordance with some aspects. Some or all of the blocks described in this example or in other examples may be performed by processing logic, which may be integral to computing device 124. Processing logic may comprise hardware (e.g., circuitry, dedicated logic, programmable logic, a processor, a processing device, a central processing unit (CPU), a system-on-chip (SoC), machine-readable memory, etc.), software (e.g., machine-readable instructions stored or executed by processing logic), or a combination thereof.

In some examples, computing device 124 may be separate from head-worn device 102. For example, computing device 124 may include a smartphone, a computer, a cloud-based server, a smart speaker, a tablet computer, or other computing device. In some examples, computing device 124 may be a wearable computing device (e.g., a wristwatch). In some examples, computing device 124 may be partially or completely integrated within head-worn device 102.

A head-worn device 102 may be worn on or in an ear 116 of a user 104. The head-worn device 102 may include in-ear sensing technologies (e.g., one or more microphones 110), and apply one or more algorithms 122 to microphone signal 118 to detect heart activity 114. As used herein, the head-worn device 102 may be worn in any appropriate manner as to create a proper seal with the user's ear, such as, for example, over or on top for an over-the-ear headphone or inserted into an ear canal for an in-ear device. For example, earbuds (in-ear headphones) may include a compressible tip (e.g., silicone or rubber) that acoustically seals off the ear canal properly worn. An over-the-ear (also known as around the ear) headphone set may have a cushion which acoustically seals against the head (rather than the ear canal). An on-ear headphone may include a cushion that presses and seals against the ear.

Head-worn device 102 may include a headphone that is worn in or on an ear 116 of a user 104. For example, the head-worn device 102 may include an earbud that is worn on the user' concha such that the earbud partially enters the ear canal of the user. In another example, the head-worn device 102 may include a shell and cushion combination that is worn over or on top of the user's ear. When worn properly, the head-worn device may create a seal against the user to acoustically separate the ultrasonic waves from the ambient environment.

The head-worn device 102 may include a microphone 110 that generates a microphone signal 118. In some examples, the head-worn device 102 may include multiple microphones, and each microphone may generate a respective microphone signal that is processed separately, as discussed.

Processing logic may cause an ultrasonic wave 128 to output from speaker 108 of the head-worn device 102. For example, processing logic may provide an audio signal 126 to drive a speaker 108. The audio signal 126 may include the ultrasonic probe signal, which is inaudible, as well as audible audio content such as, for example, music, a telephone conversation, or other audio content. Processing logic may combine a probe signal (containing one or more ultrasonic sinusoids) with an audio signal containing audio content (resulting in audio signal 126), to output the audio content and the ultrasonic wave through the speaker. The resulting audio signal 126 may be used to drive speaker 108 to output an ultrasonic wave 128 into the user's ear canal. The ultrasonic wave 128 may be sensed with microphone 110 of the device and processed as discussed. In such a manner, the device may be used as a hearing device for outputting content while also detecting a user's heart activity in the examples discussed.

At signal processing block 112, processing logic obtains the microphone signal 118 generated from the microphone of the head-worn device that senses the ultrasonic wave as it reflects off an ear of the user. Processing logic may determine a heart activity 114 of the user 104 of the head-worn device 102, based at least on the microphone signal 118. Processing logic may apply one or more algorithms 122 in processing of the microphone signal 118, to determine the heart activity 114.

As described, heart activity 114 may include movement of the user's heart 106 such as contraction of the left or right atrium and ventricle, or movement of blood through the user's heart 106. Heart activity 114 may include the expansion and contraction of arteries throughout the body, for example, arteries that are located at or around the user's ears. Heart activity 114 may include a waveform that varies in magnitude over time and/or frequency to correspond to movement of the heart or blood. In some examples, the heart activity 114 may include a heart rate of the user.

At signal processing block 112, processing logic may detect a change in phase of the ultrasonic wave as sensed in the microphone signal over a period of time to determine the heart activity 114 of the user. As the heart pumps blood around the ear canal of a user, the skin in the ear canal may deflect in response to vascular pressure waves. Slight changes in the shape of the ear canal cause slight changes in the magnitude and phase responses of a transfer function between the speaker 108 and microphone 110. Processing logic may correlate the change in phase (and/or magnitude) to a change in path length or a change in resonance (e.g., transfer function) of the ultrasonic wave from the speaker to the microphone as it reflects off of the ear of the user. The change in path length or resonance may further be correlated to the heart activity of the user.

In some examples, this period of time over which the microphone signal 118 is processed may be greater than the period of the user's heartbeat, to capture at least one full heartbeat cycle. In some examples, the period of time may be greater than a minute to capture the user's heart beats over a full minute.

Algorithm 122 may include combining (e.g., heterodyning) the microphone signal 118 with one or more features or characteristics of the probe signal (e.g., one or more probe tones that are being output.) The features or characteristics of the probe signal (which may be a real valued signal) that appear in the heterodyning signal (which may be a complex valued signal) are the frequency modulation. Those features or characteristics appear in both an output probe tone (output by the speaker) and in the microphone signal due to pick up of the output probe tone by the microphone. This feature allows separate ways to perform the heterodyning operation as discussed further below in connection FIG. 4. The result of the heterodyning operation may be filtered to isolate the change in phase of the ultrasonic wave that most correlates to heart activity. For example, the outputted ultrasonic wave may include one or more probe tones and each corresponding reflected ultrasonic wave probe tone may be heterodyned to generate a respective heterodyned signal with near-zero frequency, i.e., between zero or dc and 5 Hz, or between zero or dc and 100 Hz). Each respective heterodyned signal may be filtered to remove components other than the corresponding reflected ultrasonic wave probe tone in the respective heterodyned signal. The filtering may remove or filter out components or frequencies other than near-zero components, e.g., remove components that are above near-zero frequencies, such as above 100 Hz. Processing, including difference detection and peak detection as discussed in more detail below, may then be performed on one or more of the near-zero components, not other components at greater frequencies, to compute the heart rate.

In some examples, algorithm 122 may include an artificial neural network or other machine learning model that is trained to detect the heart activity 114 in the microphone signal based on changes in phase of the sensed ultrasonic wave. For example, an artificial neural network may be trained with a sufficiently large dataset (e.g., training data) of microphone signals with ultrasonic reflections of an inner ear, and a target output of the heart activity (e.g., a waveform of the measured heart activity corresponding to the training data) to reinforce the artificial neural network to associate the sensed ultrasonic wave in the microphone signal with the heart activity. The training data may include ground truth data that includes real measurements of heart activity.

Training an artificial neural network can involve using an optimization algorithm to find a set of weights to best map inputs (e.g., a microphone signal with sensed ultrasonic components) to outputs (e.g., heart activity). These weights may be values that represent the strength of a connection between neural network nodes of the artificial neural network. During training, the machine learning model weights can be trained to minimize the difference between a) the output generated by the machine learning model based on the input training data, and b) approved output that is associated with the training data. The input training data and target output of the training data can be described as input-output pairs, and these pairs can be used to train a machine learning model in a process that may be referred to as supervised training.

The training of the machine learning model can include using linear or non-linear regression (e.g., least squares) to optimize a cost function to reduce error of the output of the machine learning model (as compared to the approved findings of the training data). Errors are propagated back through the machine learning model, causing an adjustment of the weights which control the neural network algorithm. This process may be performed repeatedly for each recording, to adjust the weights such that the errors are reduced, and accuracy is improved. The same set of training data can be processed a plurality of times to refine the weights. The training can be completed once the errors are reduced to satisfy a threshold, which can be determined through routine test and experimentation. The trained machine learning algorithm may be trained to correlate changes in phase or changes in magnitude of the sensed ultrasonic signal to heart activity. In some examples, the machine learning algorithm may take the microphone signal and the output audio signal as input. The machine learning algorithm may be trained to recognize the relative phase information of the output ultra-sonic wave (in the output audio signal) and the reflected ultrasonic wave (in the microphone signal) and correlate this relative phase information to heart activity.

Figure 2:
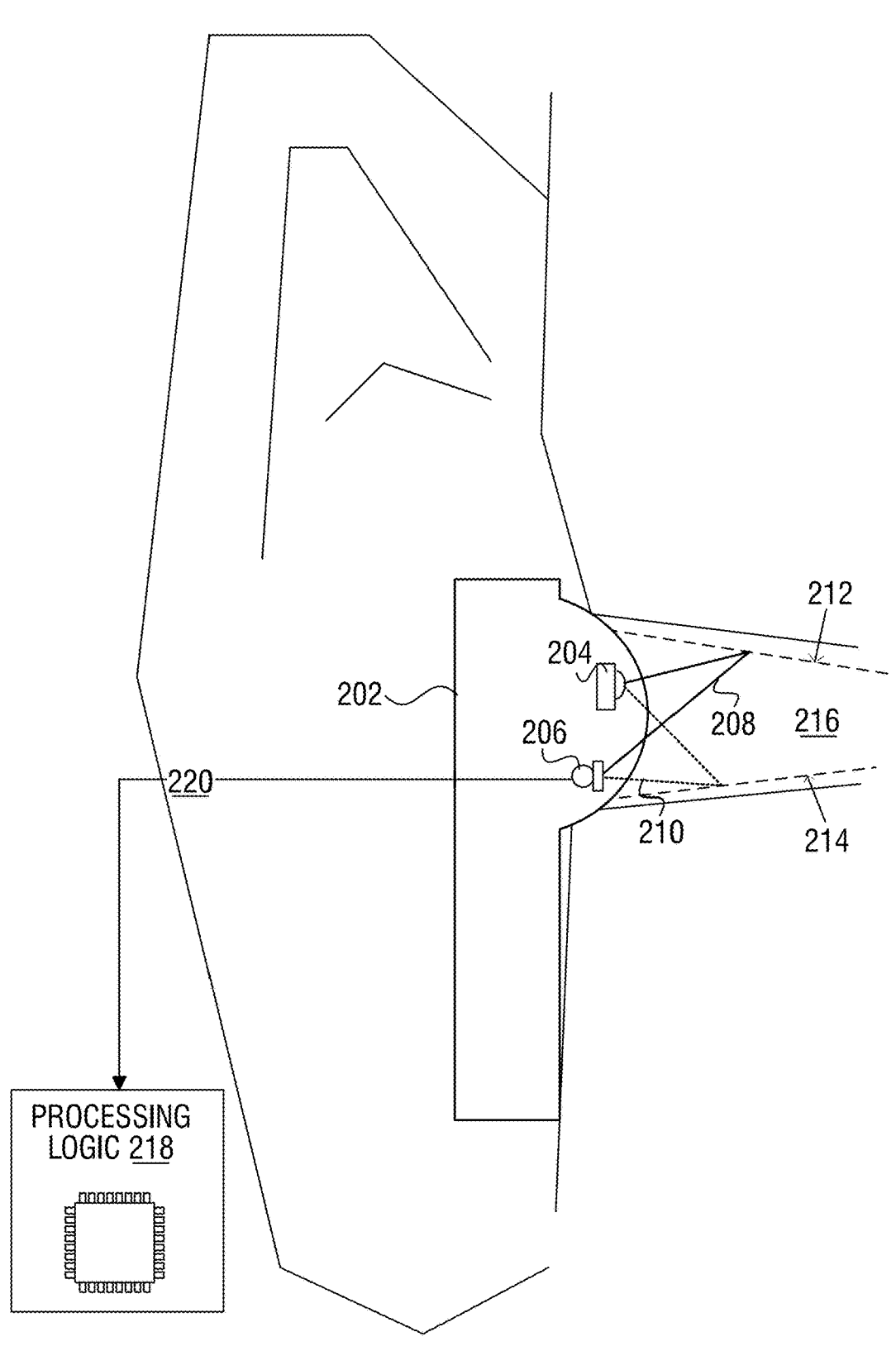
FIG. 2 shows an example of a head-worn device that may be used to determine heart activity, in accordance with some aspects.

FIG. 2 shows an example of a head-worn device 202 that may be used to determine heart activity, in accordance with some aspects. Head-worn device 102 may include an ear-bud headphone that fits in an ear canal 216 of a user.

The head-worn device 202 may emit an ultrasonic wave from speaker 204 of the head-worn device. The speaker 204 may be housed within a body of head-worn device 102 with an orientation and position to sufficiently direct acoustic energy from the speaker 204 towards the user's ear (e.g., directly into the user's ear canal 216).

Head-worn device 202 may include microphone 206 which senses the ultrasonic wave as it reflects off the ear (e.g., the user's ear canal 216). This microphone 206 may be an error microphone or an internal microphone, rather than an external microphone that senses ambient sounds directly. An internal or error microphone may be configured or arranged to directly receive the sound being produced by the headphone speaker. The microphone 206 may encode the sensed sound field in a microphone signal. Head-worn device 202 may include processing logic 218 that deter-mines heart activity of the user, based at least on the microphone signal 220, such as described below in connec-tion with FIG. 4. The heart activity may include a heart rate such as, for example, 'X' beats per minute (bpm).

Processing logic 218 may detect a change or changes in phase or in magnitude of a frequency response or resonance of the following system: from an input of the speaker, acoustically out to a surface of the ear and then acoustically back to a microphone, and then to the output of the micro-phone. Processing logic 218 may correlate this change in phase or magnitude to a change in the length of the acoustic path 208, 210 or in a resonance of the ultrasonic wave that travels from the speaker to the microphone while reflecting off of the ear of the user. Processing logic 218 may correlate the change in the length of the path 208, 210 or the change in resonance to the heart activity of the user.

For example, as the heart pumps blood around the user's ear canal, the skin 212 and 214 of the user's ear canal 216 deflects in response to vascular pressure waves. Slight changes in the shape of the ear canal (caused from these deflections) may cause slight changes in the magnitude and/or phase response of a transfer function between the speaker 204 and microphone 206. For example, a change in path length [delta_x] 208 or 210 between speaker 204 and microphone 206 may cause a corresponding change in relative phase of the sensed ultrasonic wave. The wave-length of a sound wave may be expressed as $\lambda=c/f$, where c is the speed of sound (343 m/s) and f is the frequency, which provides that:

$$\Delta\phi = \frac{2\pi f}{c} \cdot \Delta x \text{ and } \Delta x = \frac{c\Delta\phi}{2\pi f}.$$

For example, at 20 KHz, the change in skin deflection (delta_x) may be 1 mm, corresponding to a relative phase shift of 0.366 radians at the reflected ultrasonic component. Processing logic may detect such a change in relative phase and correlate this phase change to a path length. A 10 μm (microns) path length change may be correlated to 3.66 milliradians. Advantageously, such a phase shift may be measured sufficiently with microphone 206.

At signal processing block 112, processing logic may measure modulation of relative phase between transmitted probe signal (through the speaker 108) and the sensed ultrasonic wave (in microphone signal 118. The modulation of the measured phase is robust to noise and invariant to amplitude. Thus, sensing the ultrasonic signal in the micro-phone signal may provide a sufficiently robust measure of heart activity.

Further, by outputting an ultrasonic tone or tones, pro-cessing logic may sense heart activity of a user without bothering the user, given that an ultrasonic tone is inaudible, above the normal human hearing range, e.g., >20 KHz. Ambient sounds such as music and talking typically have scarce ultrasonic content. Ultrasonic tones provide excellent pulsation tracking with arbitrarily low pulse rates. A typical heart rate may be between 25-200 bpm, or 0.42-3.33 Hz.

Advantageously, the head-worn device 102 may utilize existing hardware rather than requiring additional sensors such as an accelerometer, a light sensor (e.g., a PPG sensor), or another sensor. No additional hardware is required beyond microphone 206 and speaker 204, and ability to inject probe tones into speaker output. The microphone 206 may be further used for other purposes (e.g., echo cancel-lation). Changes in amplitude response may be ignored, and a precise frequency response is not required for the speaker 204 and microphone 206 system, so long as the microphone exhibits low nonlinear distortion and a sufficient signal to noise ratio (SNR).

Figure 3:
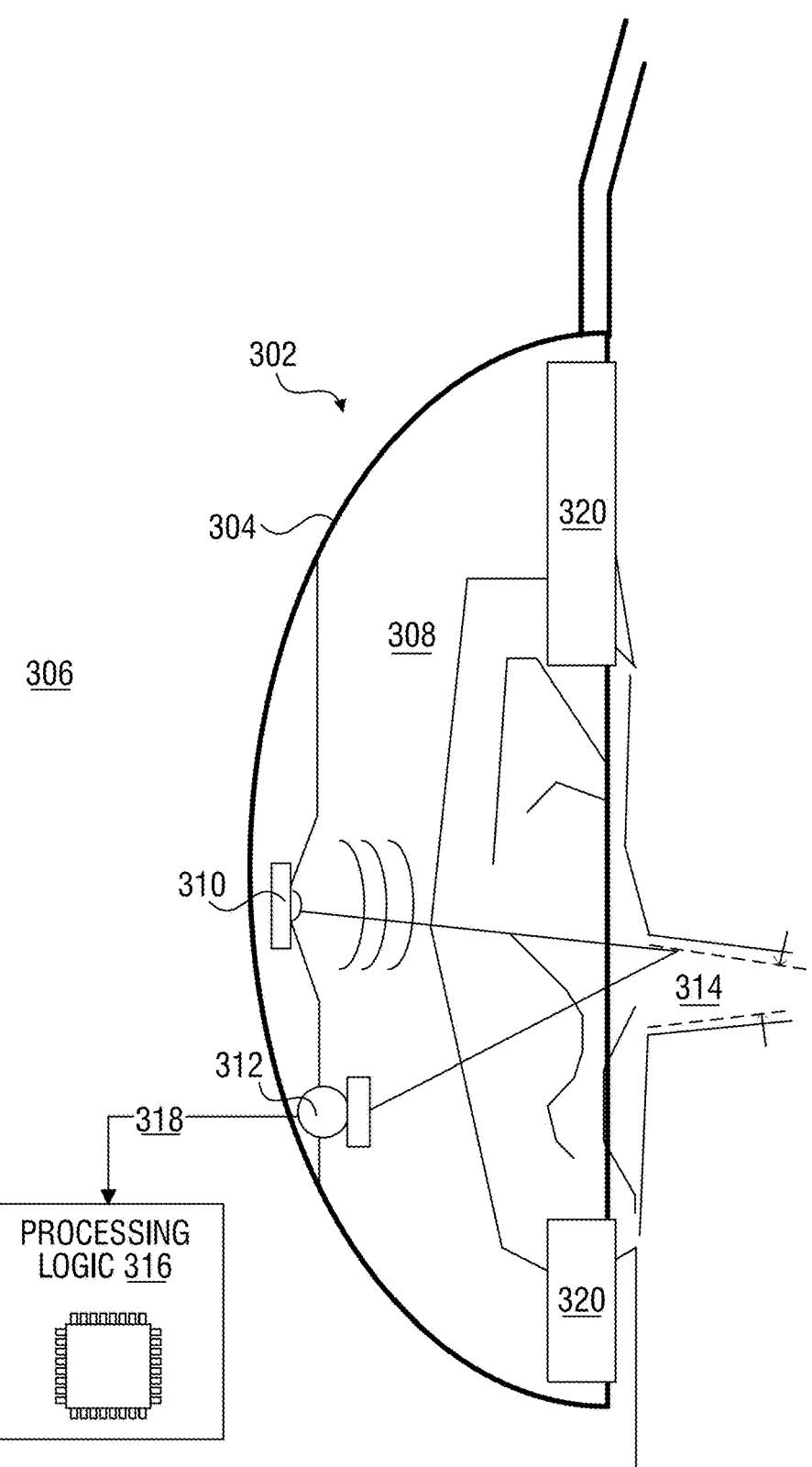
FIG. 3 shows an example of using a head-worn device to determine heart activity, in accordance with some aspects.

FIG. 3 shows an example of using a head-worn device 302 to determine heart activity, in accordance with some aspects. Head-worn device 302 may include a non in-ear headphone such as an over-the-ear or on-ear headphone. Head-worn device 302 may include a shell 304 that is worn on or over a user's ear. The shell 304 may include a cushion 320 that creates a seal between the shell 304 and the user, such that the acoustic environment 306 outside of the shell is sufficiently separated from the acoustic environment 308 inside of the shell.

Similar to other examples, the head-worn device 302 includes a speaker 310 that may be housed within the shell 304, with an orientation and position to sufficiently direct acoustic energy from the speaker 310 towards the user's ear (e.g., into the user's ear canal 314). The speaker 310 may emit an ultrasonic wave. Head-worn device 302 may include microphone 312 which senses the ultrasonic wave as it reflects off the ear (e.g., the user's ear canal 314). Micro-phone 312 may be an internal microphone or an error microphone that is arranged in the shell 304 to capture sounds from speaker 310 as well as reflected sounds from the user's ear. Processing logic 316 may determine heart activity (e.g., a heart rate or heartbeat) of the user, based at least on the microphone signal 318, as described in other sections. In some examples, processing logic 316 is integral to head-worn device 302. In other examples, processing logic 316 may be partially or completely separate from head-worn device 302.

Figure 4:
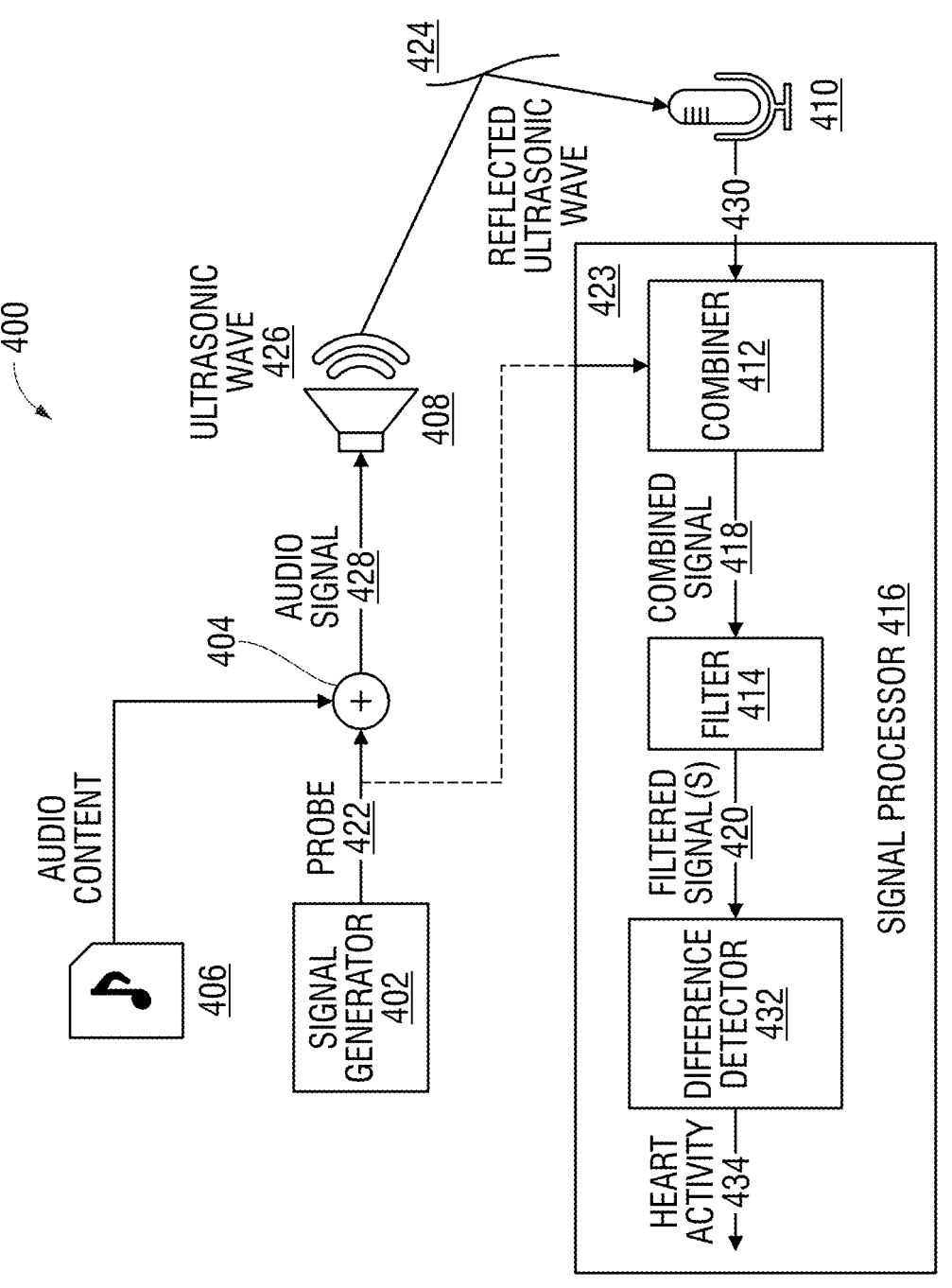
FIG. 4 shows an example workflow for determining heart activity with an ultrasonic wave, in accordance with some aspects.

FIG. 4 shows an example workflow 400 for determining heart activity with an ultrasonic wave, in accordance with some aspects. Operations and blocks of the described workflow 400 may be performed by processing logic and a head-worn device corresponding to other examples.

Probe signal generator 402 generates a probe signal 422 that includes one or more ultrasonic components. In some examples, a probe signal 422 may include multiple ultrasonic sinusoids that are summed together by the probe signal generator 402. The ultrasonic sinusoids may each have a fixed frequency and be spaced apart sufficiently in the combined probe signal, for example a probe tone may be $$p_k(n) = a_k \cos\left(\frac{2\pi f_k n}{F_s} + \phi_k\right),$$

where $a_k$ is an amplitude of $P_k^{(n)}$ and $\phi_k$ is a corresponding phase, and the probe signal may be $$tx(n) = \sum_{k=1}^{N_f} p_k(n),$$

where $N_f$ is a number of probe tones.

Due to the narrow bandwidth created by low pass filtering (described further below), sinusoidal probe tones may be placed 80-120 Hz apart (e.g., 100 Hz apart). For the ultrasonic band between 20-40 KHz, processing logic may combine up to 200 different probe tones with such spacing. For example, processing logic may determine $f_k = kf_{spacing} + f_{base}$, where $f_{base}$ is the lowest frequency in the range, e.g., 20 kHz, and $f_{spacing}$ is the spacing or the minimum spacing between the each of the probe tones (e.g., $f_{spacing} = 100$ Hz). To mitigate against a high crest factor, the relative phases $\phi_k$ may be random.

In other examples, a probe signal may include clicks, chirps, pseudorandom noise, such as maximum-length sequences, or Golay codes.

At operation 404, processing logic may combine the probe signal 422 with an audio signal of audio content 406 which may include a podcast, music, a telephone call, sound for an audiovisual work, or other audio content. The resulting audio signal 428 may contain the audio content 406 and the probe signal 422. Processing logic may drive speaker 408 to output the audio content with the ultrasonic wave 426 through the speaker 408. The ultrasonic wave 426 may be inaudible to a listener. The ultrasonic wave (which may include multiple ultrasonic components) is sensed by microphone 410 as it reflects off a surface 424 of a user's ear. Microphone 410 may be an internal or error microphone. Surface 424 may include the inner portion of the user's ear such as the user's ear canal or ear drum.

To determine heart activity 434, at the signal processor 416, processing logic measures a change (in phase and/or magnitude, in a transfer function.) It measures modulation of the relative phase between the transmitted probe signal (transmitted through the speaker 408) and the sensed ultrasonic wave (picked up in the microphone signal 430.) This is based on the microphone signal 430. In one example, the received signal rx(n) in the microphone signal may be of the form $$rx(n) = \sum_{k=1}^{N_f} \tilde{a}_k(n) \cos\left(\frac{2\pi f_k n}{F_s} + \tilde{\phi}_k(n)\right),$$

where $\tilde{a}_k(n)$ is a time-varying amplitude of a k-th received sinusoid at $f_k$, and $\overline{\phi}_k(n)$ is a corresponding time-varying phase.

Combiner 412 may combine or heterodyne the microphone signal 430 with a heterodyning signal 423 to produce a combined signal 418 (or also referred to here as a heterodyned signal.) As seen below, this operation will isolate a reflected probe signal that is contained in the microphone signal 430. The heterodyning signal 423 may be a complex valued function that is described as a "matching" ultrasonic signal that matches the real value function of the probe signal 422 which is being output by (or is driving the speaker), where the term "matching" refers to their phase variation or timing (including frequency) or frequency modulation being synchronized; for example, the heterodyning signal 423 may be a complex valued version or copy of the probe signal 422 (or probe tone) as suggested by the dotted line in FIG. 4; in another example, the heterodyning signal 423 may be a separately generated complex valued function, generated by the receiver signal processor 416 to be synchronized with the probe signal 422. For instance, a signal detector in the signal processor 416 could detect a timing offset in the microphone signal 430 and then generates a heterodyning signal based on that, where the heterodyning signal is corrected in accordance with the timing offset. The timing offset can be detected, for example in the case of a linear chirp, according to a frequency deviation, delta_f, where delta_t=delta_f/gamma where gamma is a predetermined linear chirp frequency sweep rate in Hz per second. The signal processor 416 then combines the heterodyning signal with the real valued microphone signal 430 to produce the heterodyned signal.

In the case where the probe signal 422 includes multiple fixed frequency sinusoids, the microphone signal 430 may be combined or heterodyned with each of the probe tones separately to generate multiple resulting heterodyned signals, one for each probe tone. Heterodyning may refer to multiplying a signal by the complex conjugate of the heterodyning signal. The heterodyning signal 423 may be a fixed-frequency sinusoid, a chirp, a maximum-length sequence, or other decoding sequence. For example, if a signal including a sinusoidal component at frequency f m is multiplied by the complex conjugate of a pure complex sinusoid at frequency $f_k$, the result includes a sinusoidal component at $f_m - f_k$. In particular, when $f_m = f_k$, a resulting heterodyned signal component is at frequency 0, and may be used to determine the path length of the sound wave. Changes in the path length of the sound wave can be correlated to heart activity. As such, the combined signal 418 may be comprised of a set of one or more heterodyned signals or signal components. The combined signal 418 may comprise a heterodyned signal per carrier frequency in the output ultrasonic wave. Some of the resulting signals may exhibit heart activity better than others. Those signals may be selected for determining the heart activity, while those with lower SNR may be discarded or ignored. Thus, combined signal 418 may, in some examples, exclude some components that exhibit noise or do not sufficiently exhibit heart activity.

In some aspects, processing logic may isolate each sensed or received ultrasonic component using a heterodyning demodulator and a lowpass filter 414. Each heterodyning demodulator may be expressed as:

$$h_m(n) = \exp\left(j\frac{2\pi f_m n}{F_s} + j\theta_m\right)$$

and for each m, the corresponding filtered partial probe signal sensed in the microphone signal may be expressed as the heterodyned signal:

$$q_m(n) = LPF(rx(n)h_m^*(n))$$

$$\approx \tilde{a}_m(n)\exp\left(j(\tilde{\phi}_m(n) - \theta_m)\right),$$

where LPF is the low pass filter 414, and all frequency components other than that at DC, where $f_m = f_k$, have been filtered away.

Figure 6:
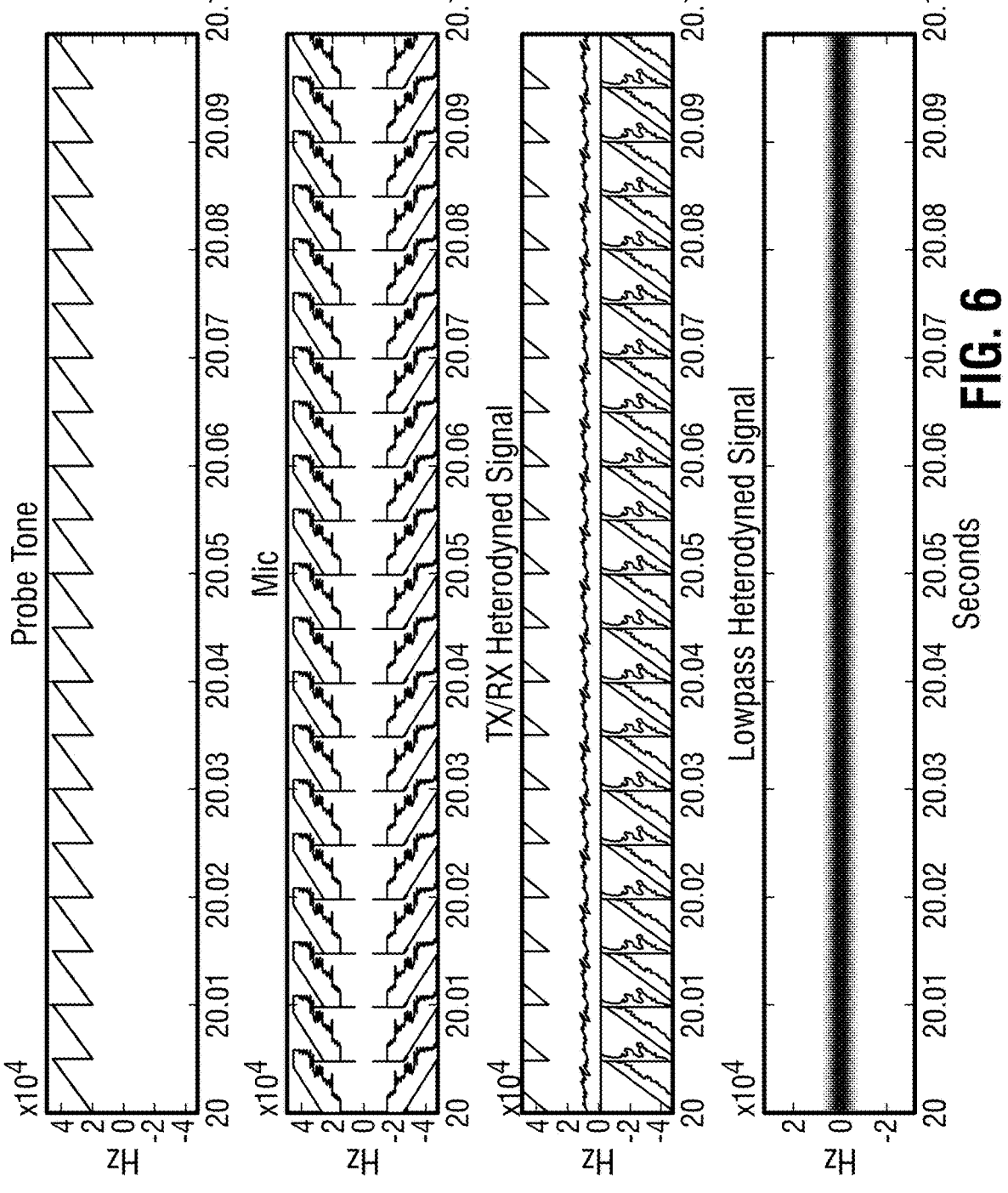
FIG. 6 shows four waveforms used in an example method for determining heart activity using a chirp probe.

In another aspect, referring now to FIG. 6, the heart rate measurement method uses an output ultrasonic wave that spans a sequence of frames, where each frame includes a probe tone whose frequency varies within the frame. In the example of the top waveform in FIG. 6, each frame is 0.05 seconds long, and the frequency of a single probe tone increases linearly from about 20 kHz to 40 kHz, and this repeats for each consecutive frame as shown. In other words, a time-varying instantaneous frequency f(k) is used for the probe signal p, and so the received signal rx, the demodulator h, and the filtered, heterodyned signal q may be expressed as:

$$p(n) = \cos\left(\sum_{k=0}^{n} \frac{2\pi f(k)}{Fs}\right),$$

$$rx(n) = \tilde{a}(n)\cos\left(\sum_{k=0}^{n} \frac{2\pi f(k)}{Fs} + \tilde{\phi}(n)\right),$$

$$h(n) = \exp\left(j\sum_{k=0}^{n} \frac{2\pi f(k)}{Fs}\right), \text{ and}$$

$$q(n) = LPF(rx(n)h^*(n))$$

An example of such a time-varying frequency modulation includes a periodically varying sawtooth frequency modulation as depicted in the probe tone waveform at the top of FIG. 6. It may be represented mathematically as:

$$f(k) = f_{lo} + (f_{hi} - f_{lo})\frac{(k \bmod N_p)}{N_p},$$

where $f_{lo}$ and $f_{hi}$ are low and high values of a range of the frequency modulation, and $N_p$ is the number of samples in a period. In the example shown, the ultrasonic chirps are periodic at a period of 5-10 milliseconds, and the frequency modulation (or chirp) sweeps linearly from 20 kHz to 40 kHz, although other combinations of frame length, frequency end points, and sweep curve, are possible.

The received signal Rx, which is picked up by the microphone, is shown next (labeled "mic" in FIG. 6) The microphone signal (produced by an internal microphone of the head-worn device) contains a reflected ultrasonic wave responsive to the output ultrasonic wave, probe tone p(n), wherein the reflected ultrasonic wave was reflected off a surface of the ear of the user. The microphone signal has a smeared spectrum as it contains the probe tone (Tx) and its reflection (e.g., convolution with an ear canal transfer function.)

Next in FIG. 6 is a plot of the heterodyned signal, which may be represented in the equations above as rx(n) multiplied by the complex conjugate of h(n). The rx(n) signal (which includes the reflected ultrasonic wave or the reflection of the probe tone in the microphone signal) is being multiplied by the complex conjugate of h(n). In one instance, the heterodyning signal may be represented by h(n). The signal or function h(n) may be an analytic signal resulting from the addition of an imaginary quadrature component from a Hilbert transform of the probe tone p(n). The probe tone p(n) may be equivalent to a real component of the heterodyning signal h(n). More generally, the reflected ultrasonic wave is said to be heterodyned by a matching time-varying frequency signal (to generate the heterodyned signal), as the term was described above.

The heterodyned signal has a near-zero frequency component and also other components that are at greater frequencies. As seen in the example shown in third plot of FIG. 6, the heterodyned signal has a flattened spectrum in which the desired component q(n) is at near-zero frequency and as such it can be isolated by applying a low pass filter (LPF) to the heterodyned signal, resulting in the plot at the bottom of FIG. 6.

In other examples of frequency modulation that may be used (instead of the one having a sawtooth instantaneous frequency as depicted in FIG. 6), the sequence of frames in the output ultrasonic wave has an instantaneous frequency like a triangle wave or a sinusoidal wave.

Each of the filtered signals $q_m(n)$ 420 may be used to provide some detailed information to determine heart activity 434. Further, the low pass filter 414 may remove interfering audio content such as from speaker 408, audio content 406, speech, or other environmental noises. The low pass filter 414 may be designed based on tradeoffs between wider bandwidth, more detail, more noise on one hand, and narrower bandwidth, less detail, less noise on the other. For example, for a typical heart rate of 60 BPM, the fundamental frequency may be 1 Hz, a filter with a 10 Hz wide bandwidth may provide sufficient detail on the periodic structure of the signal while rejecting interference. The filter may have a stop frequency that rejects noise and avoids channel overlap. In some examples, filter 414 may have a bandwidth of 10 Hz and stop band of 50 Hz. The filter 414 may include a stop band attenuation of e.g., −100 dB, in order to reject noise satisfactorily. Digital lowpass filters may include Butterworth, elliptical, Chebyshev, and other designs.

In one aspect of the method for measuring heart rate, referring now to FIG. 4, a difference detector 432 serves to compute the heart rate as follows. A time-varying phase $\bar{\phi}_m(n)$ of each filtered signal $q_m(n)$ 420 that may appear at the output of the low pass filter 414 is obtained. This may be done by taking a complex arg( ) operation of the heterodyned signal (in the combined signal 418), e.g., $\bar{\phi}_m(n) = \arg(q_m(n)) + \theta_m$ objective is to measure the pulsation of this phase signal. To avoid phase wrapping problems, it may be more convenient to work with the change in $\bar{\phi}_m(n)$ over time, e.g.

$$\Delta\tilde{\phi}_m(n) = \arg(q_m(n)q_m^*(n-1)).$$

The instantaneous phase may be expressed as $$\tilde{\phi}_m(n) = \sum_{k=1}^{n} \Delta\tilde{\phi}_m(k),$$

with the global phase removed. Next, peak detection is performed in which the difference detector 432 may find a period of a pulse waveform in the signal $\bar{\phi}_m(n)$ or $\Delta\bar{\phi}_m(n)$, by determining when each peak occurs. In some examples, this may include computing the zero crossings of $\Delta\bar{\phi}_m(n)$. Other techniques can be applied to detect peaks and/or the period of the pulse waveform. Once peak locations in time $\tau_\ell$ are determined, where $\tau_\ell$ is the time of the $\ell$-th peak, the instantaneous pulse period is the time distance or time interval between successive or consecutive peaks, $$\Delta T_\ell = T_\ell - T_{\ell-1}.$$

The heart rate may then be determined to be $$60/\Delta T_\ell$$

beats per minute.

In another aspect of the method for measuring or computing the heart rate, referring now to the equations above for the response q(n) and to the chirp embodiment of FIG. 6, the difference detector 432 (see FIG. 4) is configured to compute a change or difference $\Delta q(n)$ in the response q(n) relative to a time $n-\Delta T$ in the past. One way is to measure $\Delta q(n)$ as a subtraction:

$$\Delta q(n) \Delta q(n) = q(n) - q(n - \Delta t)$$

Another way, is to measure the response change as a division or ratio $$\Delta q(n) = q(n) / q(n - \Delta t)$$

The response difference may also be normalized for convenience, e.g., $$\Delta q(n) = \frac{q(n) - q(n - \Delta t)}{q(n - \Delta t)}$$
$$= \frac{q(n)}{q(n - \Delta t)} - 1.$$

In some aspects, it is convenient to use $\Delta t = N_p$, the periodicity of the frequency modulation, so that each sample of q(n) is compared with a corresponding sample from one period in the past. In one aspect, q(n) is computed at each time index m for each respective frequency index k given by $\chi[m, k]$ where the index m is a frame time and the index k is time within the frame of length $N_p$. This $\Delta t$ need not be a constant but for practical convenience it may be a constant.

Figure 7:
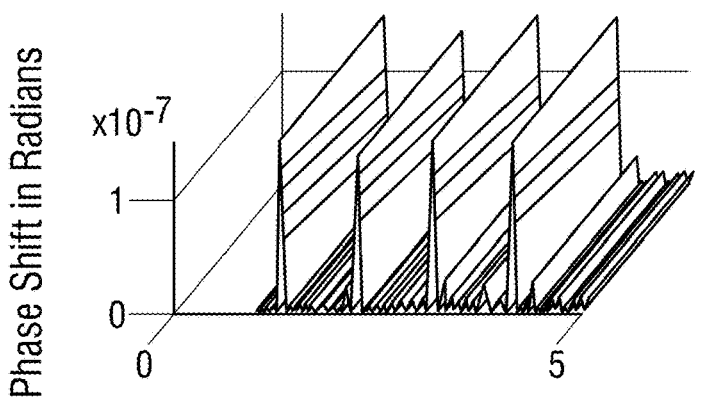
FIG. 7 is a plot of the change values produced by the difference detector for a chirp-based method, and the resulting time series of heartbeat values.
Figure 7:
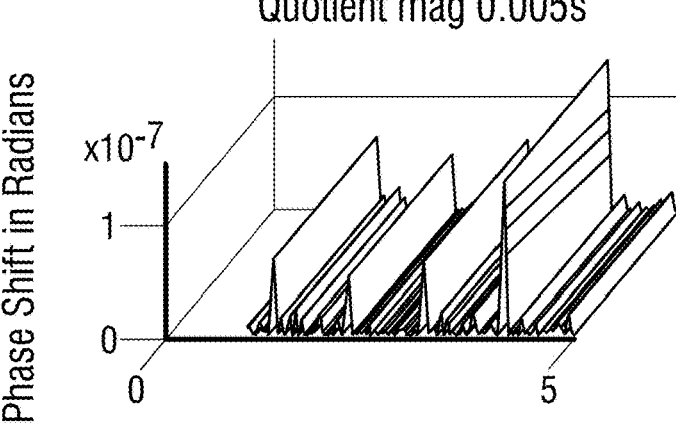
Figure 7:
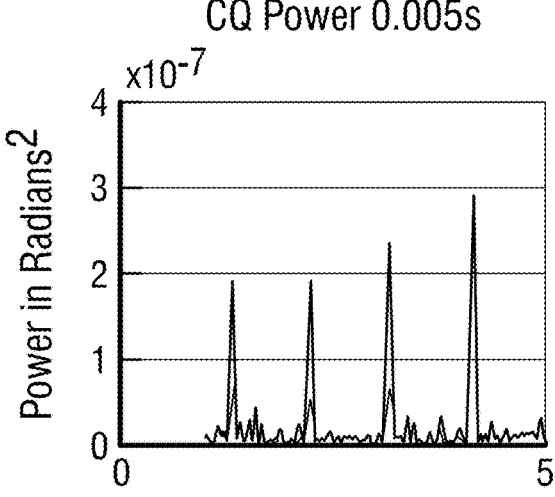

More generally then, the change in response q(n) is measured (by the difference detector 432) detecting a time sequence of difference values, such as CQ[m, k], wherein each difference value represents a difference in phase or a difference in magnitude of the heterodyned signal between one frame and an earlier frame of the heterodyned signal. FIG. 7 shows a plot of CQ[m, k] for an example quotient phase, and a plot of CQ[m, k] for an example quotient magnitude, where the time sequence covers at least two seconds (here, five seconds as an example.) The difference detector 432 then detects the peaks in the time sequence of difference values, which can be seen in the power plot at the bottom of FIG. 7. The heart rate is then taken to be proportional to a time interval separating a pair of adjacent peaks.

Viewed another way, the difference detector 432 is computing a time sequence of differences in frequency response or differences in spectrum. Each frequency response or spectrum difference is a difference between i) a frequency response or spectrum computed for one frame and ii) the frequency response or spectrum computed for an earlier frame, of the heterodyned signal. The difference detector 432 will then detect the peaks in the time sequence and provides the heart rate as a number that is proportional to the time intervals separating one or more adjacent pairs of the peaks.

Viewed in yet another way, the difference detector 432 is generating a time sequence of change values, wherein each change value represents a change in the heterodyned signal between respective (e.g., adjacent) frames of the heterodyned signal; and is detecting a plurality of peaks in the time sequence of change values, wherein the heart rate is then given or output as being proportional to the time intervals separating one or more adjacent pairs of peaks in the plurality of peaks. For instance, generating the time sequence of change values comprises: for a current chirp frame, computing a plurality of difference values, wherein each difference value indicates a difference in frequency response computed at a respective, single frequency, between the current frame and a previous frame; and summing the plurality of difference values (e.g., across all of the frequencies in the chirp frame) to produce a sum that represents one of the change values in the time sequence. If this sum is sufficiently small (smaller than some threshold, close to zero), then this may be interpreted to mean that the there is no change between the previous frame and the current frame. But if the sum is larger than the threshold, then this is interpreted to mean that there is a change between the previous frame and the current frame. In both cases, the change is quantified and stored as a sample for the current frame. This process is repeated for adjacent pairs of frames, resulting in a sequence of quantified change samples (e.g., power values) such as shown in bottom plot of FIG. 7. A peak detection process is also being performed concurrently to detect the peaks which are interpreted to represent heart beats.

In some aspects, the heart activity 434 is a heart rate. In some aspects, the heart activity 434 may be displayed or presented to a user. Additionally, or alternatively, the heart activity 434 may be used with other algorithms to detect an indication (e.g., an elevated risk) of heart pathology. A heart pathology may include an aortic murmur, brady cardia, tachycardia, aortic stenosis, mitral regurgitation, aortic regurgitation, mitral stenosis, patent ductus arteriosus, or other heart pathology. The heart pathology may include an abnormal heart activity, heart rhythm, or heartbeat, such as heart activity that deviates from a normal or healthy heart activity in one or more cardiac cycles.

In such a manner, processing logic may leverage a multitone approach. Due to narrowband carriers and slowly time-varying phase modulation, each probe response can be bandpass isolated to <50 Hz of bandwidth. Each demodulated carrier band may be subsampled to 100 Hz, vs 96 KHz. Up to 200 or more simultaneous probe tones can be used to measure pulsation with statistically independent noise per channel. A maximum-likelihood technique could be used to combine independent pulsation estimates across the many probe carrier frequencies. As such, the technique may be more resistant or immune to noise in the microphone or ear canal frequency response for the detection of heart activity.

Figure 5:
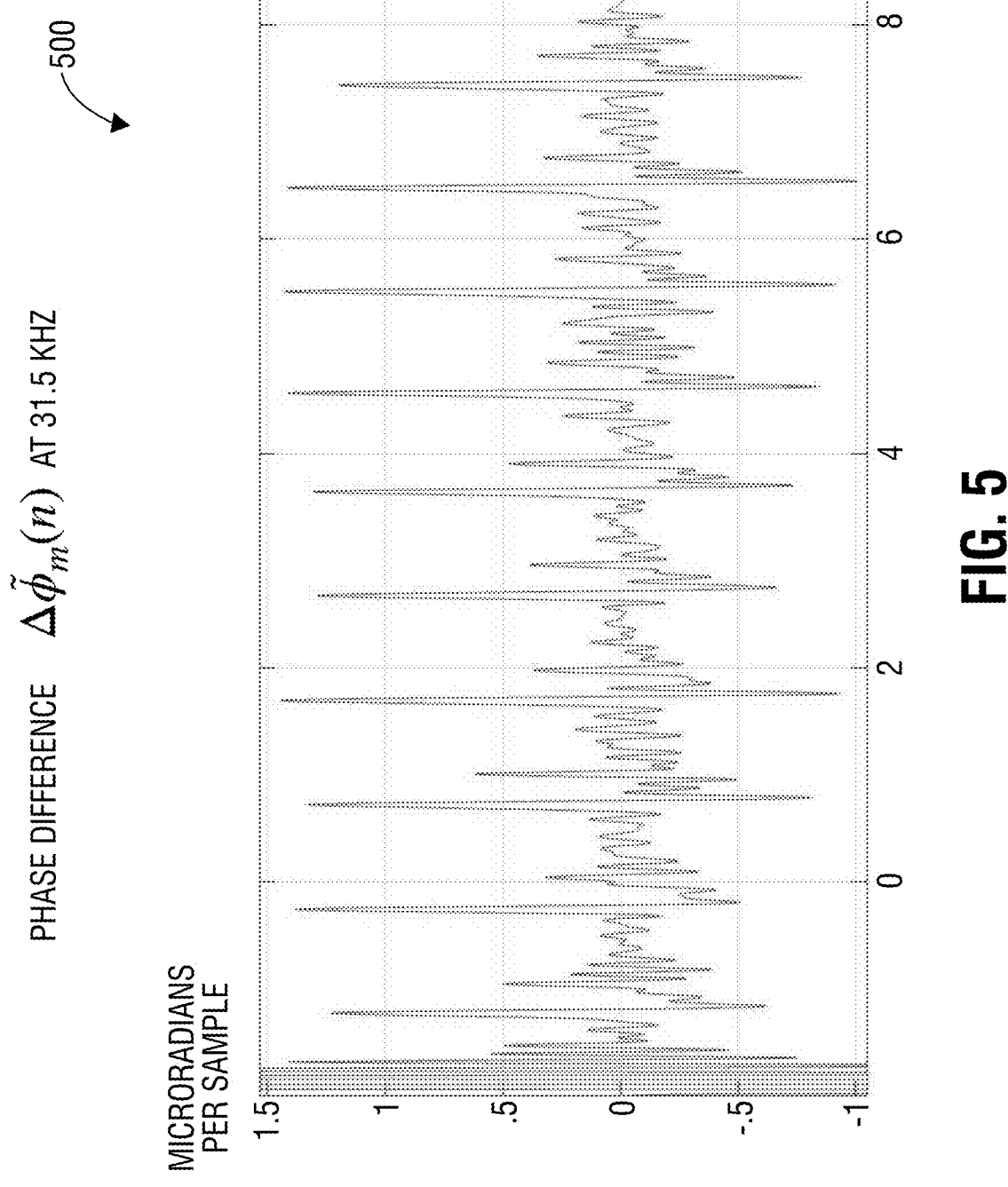
FIG. 5 depicts a graph depicting an indication of heart activity using a microphone signal, in accordance with some aspects.

FIG. 5 is a graph 500 depicting an indication of heart activity measured using a microphone signal, in accordance with some aspects described here. Graph 500 shows a phase difference $\Delta\bar{\phi}_m(n)$, though alternatively $\Delta q(m)$ could be used, which is shown to vary in microradians (in the Y-axis) over time (in the X-axis). This difference may be extracted at the difference detector 432 as described above in connection with FIG. 4. An aspect of this technique is that the phase signal $\bar{\phi}_m(n)$ is small, like milliradians. Although small, under nominal operating conditions, the signal to noise ratio is empirically sufficient (e.g., measurable). In this plot of measured data, with a phase $\bar{\phi}_m(n)$ (measured from a 31.5 KHz carrier probe tone, an excursion of approximately 5 milliradians may be measured. This translates to an 8.6 micron excursion in path length. The magnitude of $\Delta\bar{\phi}_m(n)$ is expected to be small. In the presence of disruption, noise, or no signal, however, the phase becomes random, and the RMS phase difference jumps to many orders of magnitude larger than the nominal microradians. Thus, one or more conditions may cause the tracking of heart activity to fail. This allows one detection heuristic to be that $|\Delta\bar{\phi}_m(n)|$ be less than a numerically small threshold like 1e-6 or 1e-5. If larger, then this may indicate that an anomaly is present and the sensed microphone signal (or a given heterodyned probe tone) is not to be relied on.

As described above, a computing device has a processor that is configured to cause an ultrasonic wave to output from a speaker of a head-worn device when the head-worn device is worn on or in an ear of a user; obtain a microphone signal of a microphone of the head-worn device that receives a reflected ultrasonic wave responsive to the outputted ultrasonic wave; and determine a heart activity of the user of the head-worn device, based at least on the microphone signal. The heart activity may be detected by detecting surface movement of the ear, which in may be detected based on determining a change in a frequency response of the system in which the output ultrasonic wave and the received reflected ultrasonic wave are generated and detected. The frequency response may be measured using clicks, chirps, or pseudorandom noise (in the output ultrasonic wave.) The heart activity may be detected by heterodyning the reflected ultrasonic wave with a heterodyning signal, to generate a heterodyned signal with a near-zero frequency component. The heterodyned signal includes a relative phase between the outputted ultrasonic wave and the reflected ultrasonic wave, or a sensed time of flight of between the outputted ultrasonic wave and the reflected ultrasonic wave, or a frequency response (e.g., a transfer function) of the system in which the outputted ultrasonic wave and the reflected ultrasonic wave are generated and detected. In one aspect, the output ultrasonic wave may include one or more probe tones, and each corresponding reflected ultrasonic wave probe tone is heterodyned to generate a respective heterodyned signal with near-zero frequency. Each respective heterodyned signal is filtered to filter out components other than its near-zero component, and then a difference detection over time is performed on the near-zero component to determine the heart activity. In one aspect, the one or more probe tones include at least one of: a plurality of fixed frequency sinusoids or one or more frequency sweep tones. In another aspect, causing the ultrasonic wave to output from the speaker of the head-worn device is achieved by combining one or more probe tones with audio content resulting in an audio signal and driving the speaker with the audio signal. The heart activity of the user may be determined by detecting adjacent peaks in a relative phase between the output ultrasonic wave and reflected ultrasonic wave, and determining a heart rate based on (e.g., proportional to) a time interval between the peaks.

In another aspect of the disclosure also described above, a head-worn device has a speaker, a microphone and a processor configured to: cause an ultrasonic wave to output from the speaker of the head-worn device; obtain a microphone signal of a microphone of the head-worn device that senses a reflected ultrasonic wave responsive to the outputted ultrasonic wave; and determine a heart activity of a user of the head-worn device, based at least on the reflected ultrasonic wave characterized in the microphone signal. The speaker and the microphone may be arranged in an earbud of the head-worn device. Alternatively, the speaker and the microphone may be arranged in a shell that is worn on or over an ear of the user.

Figure 8:
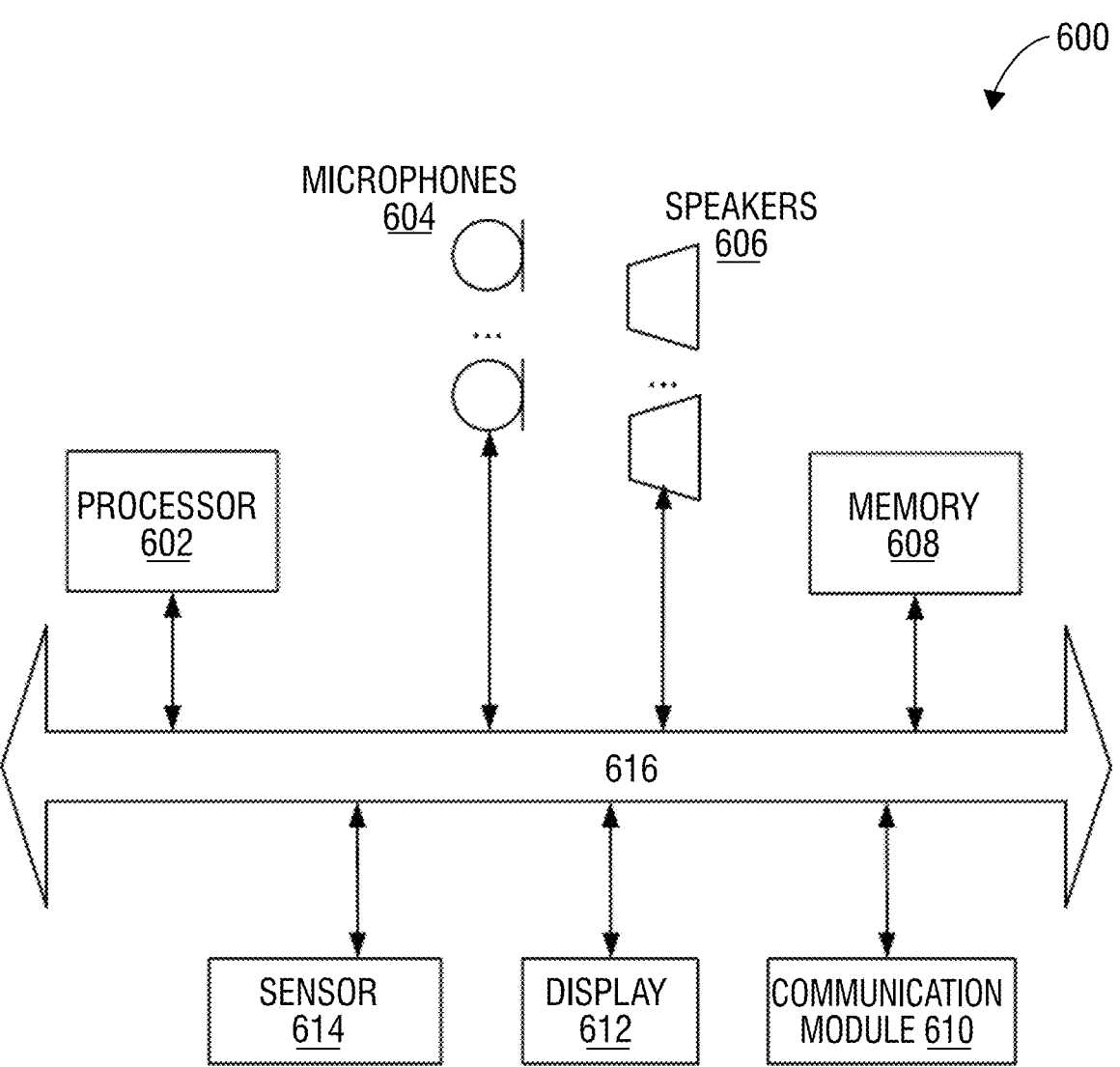
FIG. 8 illustrates an example of an audio processing system, in accordance with some aspects.

FIG. 8 illustrates an example of an audio processing system 600, in accordance with some aspects. The audio processing system can be a device such as, for example, a desktop computer, a tablet computer, a smartphone, a computer laptop, a smart speaker, a media player, a household appliance, a headphone set, a head mounted display (HMD), a watch, smart glasses, an infotainment system for an automobile or other vehicle, or another computing device. The system can be configured to perform the method and processes described in the present disclosure.

Although various components of an audio processing system are shown that may be incorporated into headphones, speaker systems, microphone arrays and entertainment systems, this illustration is merely one example of a particular implementation of the types of components that may be present in the audio processing system. This example is not intended to represent any particular architecture or manner of interconnecting the components as such details are not germane to the aspects herein. It will also be appreciated if other types of audio processing systems that have fewer or more components than shown can also be used. Accordingly, the processes described herein are not limited to use with the hardware and software shown.

The audio processing system can include one or more buses 616 that serve to interconnect the various components of the system. One or more processors 602 are coupled to bus as is known in the art. The processor(s) may be microprocessors or special purpose processors, system on chip (SOC), a central processing unit, a graphics processing unit, a processor created through an Application Specific Integrated Circuit (ASIC), or combinations thereof. Memory 608 can include Read Only Memory (ROM), volatile memory, and non-volatile memory, or combinations thereof, coupled to the bus using techniques known in the art. Sensors 614 can include an IMU and/or one or more cameras (e.g., RGB camera, RGBD camera, depth camera, etc.) or other sensors described herein. The audio processing system can further include a display 612 (e.g., an HMD, or touchscreen display).

Memory 608 can be connected to the bus and can include DRAM, a hard disk drive or a flash memory or a magnetic optical drive or magnetic memory or an optical drive or other types of memory systems that maintain data even after power is removed from the system. In one aspect, the processor 602 retrieves computer program instructions stored in a machine readable storage medium (memory) and executes those instructions to perform operations described herein.

Audio hardware, although not shown, can be coupled to the one or more buses in order to receive audio signals to be processed and output by speakers 606. Audio hardware can include digital to analog and/or analog to digital converters. Audio hardware can also include audio amplifiers and filters. The audio hardware can also interface with microphones 604 (e.g., microphone arrays) to receive audio signals (whether analog or digital), digitize them when appropriate, and communicate the signals to the bus.

Communication module 610 can communicate with remote devices and networks through a wired or wireless interface. For example, communication modules can communicate over known technologies such as TCP/IP, Ethernet, Wi-Fi, 3G, 4G, 5G, Bluetooth, ZigBee, or other equivalent technologies. The communication module can include wired or wireless transmitters and receivers that can communicate (e.g., receive and transmit data) with networked devices such as servers (e.g., the cloud) and/or other devices such as remote speakers and remote microphones.

It will be appreciated that the aspects disclosed herein can utilize memory that is remote from the system, such as a network storage device which is coupled to the audio processing system through a network interface such as a modem or Ethernet interface. The buses can be connected to each other through various bridges, controllers and/or adapters as is well known in the art. In one aspect, one or more network device(s) can be coupled to the bus. The network device(s) can be wired network devices (e.g., Ethernet) or wireless network devices (e.g., Wi-Fi, Bluetooth). In some aspects, various aspects described (e.g., simulation, analysis, estimation, modeling, object detection, etc.,) can be performed by a networked server in communication with the capture device.

Various aspects described herein may be embodied, at least in part, in software. That is, the techniques may be carried out in an audio processing system in response to its processor executing a sequence of instructions contained in a storage medium, such as a non-transitory machine-readable storage medium (e.g., DRAM or flash memory). In various aspects, hardwired circuitry may be used in combination with software instructions to implement the techniques described herein. Thus, the techniques are not limited to any specific combination of hardware circuitry and software, or to any particular source for the instructions executed by the audio processing system.

In the description, certain terminology is used to describe features of various aspects. For example, in certain situations, the terms "module," "processor," "unit," "renderer," "system", "device", "filter", "engine", "block", "detector", "isolator", "extractor", "generator", "model", and "component", are representative of hardware and/or software configured to perform one or more processes or functions. For instance, examples of "hardware" include, but are not limited or restricted to an integrated circuit such as a processor (e.g., a digital signal processor, microprocessor, application specific integrated circuit, a micro-controller, etc.). Thus, different combinations of hardware and/or software can be implemented to perform the processes or functions described by the above terms, as understood by one skilled in the art. Of course, the hardware may be alternatively implemented as a finite state machine or even combinatorial logic. An example of "software" includes executable code in the form of an application, an applet, a routine or even a series of instructions. As mentioned above, the software may be stored in any type of machine-readable medium.

Some portions of the preceding detailed descriptions have been presented in terms of algorithms and symbolic representations of operations on data bits within a computer memory. These algorithmic descriptions and representations are the ways used by those skilled in the audio processing arts to convey the substance of their work most effectively to others skilled in the art. An algorithm is here, and, conceived to be a self-consistent sequence of operations leading to a desired result. The operations are those requiring physical manipulations of physical quantities. It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of an audio processing system, or similar electronic device, that manipulates and transforms data represented as physical (electronic) quantities within the system's registers and memories into other data similarly represented as physical quantities within the system memories or registers or other such information storage, transmission or display devices.

The processes and blocks described herein are not limited to the specific examples described and are not limited to the specific orders used as examples herein. Rather, any of the processing blocks may be re-ordered, combined, or removed, performed in parallel or in serial, as desired, to achieve the results set forth above. The processing blocks associated with implementing the audio processing system may be performed by one or more programmable processors executing one or more computer programs stored on a non-transitory computer readable storage medium to perform the functions of the system. All or part of the audio processing system may be implemented as, special purpose logic circuitry (e.g., an FPGA (field-programmable gate array) and/or an ASIC (application-specific integrated circuit)). All or part of the audio system may be implemented using electronic hardware circuitry that include electronic devices such as, for example, at least one of a processor, a memory, a programmable logic device or a logic gate. Further, processes can be implemented in any combination of hardware devices and software components.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

While certain aspects have been described and shown in the accompanying drawings, it is to be understood that such aspects are merely illustrative of and not restrictive, and the disclosure is not limited to the specific constructions and arrangements shown and described, since various other modifications may occur to those of ordinary skill in the art.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

It is well understood that the use of personally identifiable information should follow privacy policies and practices that are recognized as meeting or exceeding industry or governmental requirements for maintaining the privacy of users. In particular, personally identifiable information data should be managed and handled so as to minimize risks of unintentional or unauthorized access or use, and the nature of authorized use should be clearly indicated to users.

What is claimed is:

1. A method for measuring a heart rate of a user, the method comprising:

causing an output ultrasonic wave to be output from a speaker of a head-worn device when the head-worn device is worn on or in an ear of a user;

obtaining a microphone signal of a microphone of the head-worn device that receives a reflected ultrasonic wave responsive to the output ultrasonic wave; and determining a heart rate of the user of the head-worn device, based at least on the microphone signal wherein determining the heart rate comprises detecting a surface movement of the ear of the user based on the reflected ultrasonic wave in the microphone signal, the surface movement of the ear being correlated to heart activity of the user, wherein detecting the surface movement of the ear comprises:

heterodyning the reflected ultrasonic wave to generate a heterodyned signal with near-zero frequency, and processing the heterodyned signal to detect a relative phase between the output ultrasonic wave and the reflected ultrasonic wave, or a sensed time of flight between the output ultrasonic wave.

2. The method of claim 1, wherein the surface movement of the ear is detected based on detecting a change in a relative phase between the output ultrasonic wave and the reflected ultrasonic wave in the microphone signal over time and wherein the change in the relative phase is correlated to a change in resonance of the reflected ultrasonic wave from the speaker to the microphone as it reflects off of the ear of the user.

3. The method of claim 1, wherein the surface movement of the ear is detected based on a change in a time of flight between the output ultrasonic wave and the reflected ultrasonic wave, over time.

4. The method of claim 1, wherein the output ultrasonic wave includes a plurality of probe tones and heterodyning the reflected ultrasonic wave generates a plurality of heterodyned signals with near-zero frequency.

5. The method of claim 4, further comprising low pass filtering each of the plurality of heterodyned signals and then performing peak detection to determine the heart rate.

6. The method of claim 4, wherein the plurality of probe tones is a plurality of fixed frequency sinusoids or one or more frequency sweep tones.

7. The method of claim 4, wherein causing the output ultrasonic wave to output from the speaker of the head-worn device comprises combining the plurality of probe tones with audio content resulting in an audio signal and driving the speaker with the audio signal.

8. The method of claim 1, wherein determining the heart rate of the user includes applying a machine learning algorithm to the microphone signal to determine the heart rate of the user.

9. The method of claim 1, wherein determining the heart rate of the user includes detecting peaks in a relative phase between the output ultrasonic wave and the reflected ultrasonic wave and determining the heart rate based on a time interval between the peaks.

10. A computing device comprising a processor configured to:

cause an output ultrasonic wave to be output from a speaker of a head-worn device when the head-worn device is worn on or in an ear of a user;

obtain a microphone signal of a microphone of the head-worn device that receives a reflected ultrasonic wave responsive to the output ultrasonic wave; and determine a heart activity of the user of the head-worn device, based at least on the microphone signal by detecting a surface movement of the ear, the surface movement being correlated to heart activity, wherein detecting the surface movement comprises:

heterodyning the reflected ultrasonic wave to generate a heterodyned signal with near-zero frequency, and processing the heterodyned signal to detect a relative phase between the output ultrasonic wave and the reflected ultrasonic wave, or a sensed time of flight between the output ultrasonic wave and the reflected ultrasonic wave.

11. The computing device of claim 10 wherein the surface movement of the ear is detected based on detecting a change in a relative phase between the output ultrasonic wave and the reflected ultrasonic wave in the microphone signal over time and wherein the change in the relative phase is correlated to a change in path length or a resonance of the reflected ultrasonic wave from the speaker to the microphone as it reflects off of the ear of the user.

12. The computing device of claim 10, wherein the surface movement of the ear is detected based on a change in a time of flight between the output ultrasonic wave and the reflected ultrasonic wave, over time.

13. An article of manufacture comprising machine-readable memory having stored therein instructions that configure a processor to:

cause an output ultrasonic wave to be output from a speaker of a head-worn device when the head-worn device is worn on or in an ear of a user;

obtain a microphone signal of a microphone of the head-worn device that receives a reflected ultrasonic wave responsive to the output ultrasonic wave; and determine a heart activity of the user of the head-worn device, based at least on the microphone signal by detecting a surface movement of the ear, the surface movement being correlated to heart activity, wherein detecting the surface movement comprises:

heterodyning the reflected ultrasonic wave to generate a heterodyned signal with near-zero frequency, and processing the heterodyned signal to detect a relative phase between the output ultrasonic wave and the reflected ultrasonic wave, or a sensed time of flight between the output ultrasonic wave and the reflected ultrasonic wave.

14. The article of manufacture of claim 13 wherein the surface movement of the ear is detected based on detecting a change in the relative phase between the output ultrasonic wave and the reflected ultrasonic wave over time and wherein the change in the relative phase is correlated to a change in resonance of the reflected ultrasonic wave from the speaker to the microphone as it reflects off of the ear of the user.

15. The article of manufacture of claim 13 wherein the surface movement of the ear is detected based on detecting a change in the time of flight between the output ultrasonic wave and the reflected ultrasonic wave, over time.

16. The article of manufacture of claim 13 wherein the output ultrasonic wave includes a plurality of probe tones and heterodyning the reflected ultrasonic wave generates a plurality of heterodyned signals with near-zero frequency.

17. The article of manufacture of claim 16 wherein the instructions further configure the processor to low pass filter each of the plurality of heterodyned signals and then perform peak detection to determine a heart rate.

18. The article of manufacture of claim 16 wherein the plurality of probe tones is a plurality of fixed frequency sinusoids or one or more frequency sweep tones.

19. The article of manufacture of claim 16 wherein causing the output ultrasonic wave to output from the speaker of the head-worn device comprises combining the plurality of probe tones with audio content resulting in an audio signal and driving the speaker with the audio signal.

20. The article of manufacture of claim 13 wherein determining the heart activity of the user comprises detecting peaks in the relative phase between the output ultrasonic wave and the reflected ultrasonic wave and determining a heart rate based on a time interval between the peaks.

* * * * *